United States Patent [19]

Herdle

[11] Patent Number: 4,503,250

[45] Date of Patent: Mar. 5, 1985

[54] PREPARATION OF POLYALKYLENE POLYAMINES

[75] Inventor: William B. Herdle, Greenburgh, N.Y.

[73] Assignee: Union Carbide Corporation, Danbury, Conn.

[21] Appl. No.: 532,767

[22] Filed: Sep. 16, 1983

Related U.S. Application Data

[63] Continuation of Ser. No. 307,228, Sep. 30, 1981, abandoned.

[51] Int. Cl.$^3$ ............................................. C07C 85/06
[52] U.S. Cl. .................................... 564/479; 564/478
[58] Field of Search ....................... 564/478, 479, 498

[56] References Cited

U.S. PATENT DOCUMENTS

| | | | |
|---|---|---|---|
| 2,812,333 | 11/1957 | Steele | 564/487 |
| 3,038,904 | 6/1962 | Godfrey | 564/498 |
| 4,272,455 | 6/1981 | Cook et al. | 564/503 |
| 4,324,917 | 4/1982 | McConnell | 564/479 |

OTHER PUBLICATIONS

*Handbook of Chemistry and Physics*, 63rd Edition (1982-1983), CRC Press, Inc., Boca Raton, Fl., p. F-171.

Primary Examiner—Paul F. Shaver
Attorney, Agent, or Firm—Norman L. Balmer

[57] ABSTRACT

A process is provided for preparing predominantly linear polyalkylene polyamines which comprises reacting ammonia or an alkyleneamine compound having two primary amino groups or mixtures thereof with an alcohol or an alkanolamine compound having a primary amino group and a primary or secondary hydroxyl group or mixtures thereof in the presence of a derivative of carbonic acid at a temperature at which the reaction will proceed under pressures sufficient to maintain the reaction mixture substantially in a liquid phase.

10 Claims, No Drawings

PREPARATION OF POLYALKYLENE POLYAMINES

This application is a continuation of application Ser. No. 307,228, filed Sept. 30, 1981, now abandoned.

TECHNICAL FIELD

This invention relates to the preparation of polyalkylene polyamines and, more particularly, to a catalytic, liquid phase process for producing predominantly linear polyalkylene polyamines with low heterocyclic amine content.

BACKGROUND ART

Heretofore, the conventional method for producing polyalkylene polyamine compounds and particularly polyethylene polyamine compounds such as diethylenetriamine, triethylenetetramine, and the higher homologs was to react an alkyl halide, e.g. ethylene dichloride, with ammonia or an amine compound such as ethylene diamine and the like at elevated temperatures and pressures. These methods, while widely practiced and capable of producing commercially acceptable yields of predominantly linear polyethylene polyamines with varying amounts of heterocyclic amines, have been found to present serious disadvantages.

Separation and recovery of the polyamines is difficult and the process presents a serious problem of disposal of halide salt by-products. Moreover, the ability to select the linear and heterocyclic polyamines that are produced is somewhat limited.

Several procedures have been suggested as, for example, disclosed in U.S. Pat. No. 3,714,259 to Lichtenwalter et al, and U.S. Pat. Nos. 4,036,881 and 4,044,053 to Brennan et al, for preparing predominantly linear polyamines which do not entail the halide salt disposal problem, but ability to control the composition of the mixture of the linear and heterocyclic polyamines produced thereby is limited and/or they involve the use of relatively expensive catalysts and procedures. It would be desirable, therefore, if a process or processes could be developed which achieved greater flexibility in the selection of the linear polyethylene polyamines that could be prepared and/or involved the use of less complex and less expensive materials and process procedures.

DISCLOSURE OF INVENTION

In accordance with the present invention there is provided a process for preparing predominantly linear polyalkylene polyamines which comprises reacting ammonia or an alkyleneamine compound having two primary amino groups or mixtures thereof with an alcohol having primary or secondary hydroxyl groups or an alkanolamine compound having a primary or secondary amino group and a primary or secondary hydroxyl group or mixtures thereof in the presence of a derivative of carbonic acid at a temperature at which the reaction will proceed under pressures sufficient to maintain the reaction mixture substantially in a liquid phase. The polyalkylene polyamines thus produced are then recovered from the resulting reaction mixture.

It has been discovered that predominantly linear polyalkylene polyamines in good yields and with a significant degree of flexibility and selectivity depending on the particular reactants employed can be prepared by carrying out the reaction in the presence of even small amounts of a derivative of carbonic acid, though stoichiometric amounts of such materials may also be employed.

DETAILED DESCRIPTION

In accordance with the process of the invention predominantly linear polyalkylene polyamines are produced by reacting an alkyleneamine or ammonia or mixtures of the same with an alcohol or an alkanolamine or mixtures of the same in the presence of a derivative of carbonic acid in a substantially liquid phase reaction system at elevated temperatures at which the reaction will proceed. The presence of a derivative of carbonic acid in the reaction system is essential. The polyalkylene polyamines produced by the process are then recovered from the reaction mixture, the particular method to be used depending upon the type of polyamines prepared and the composition of the product mixture prepared by the particular reactants employed. The process of the invention provides sufficient flexibility to enable a significant degree of selection as to the type of linear polyalkylene polyamines that are produced.

The alkanolamine compounds which can be generally employed in the present invention include those represented by the formula:

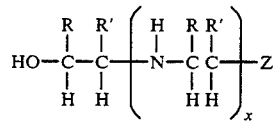

wherein R and R' are the same or different and are hydrogen or a lower alkyl radical, x is an integer from 0 to about 6 and, preferably, from 0 to about 3, and Z is OH or $NH_2$. Exemplary suitable compounds are monoethanolamine, diethanolamine, mixtures of mono- and diethanolamine, N-(2-aminoethyl)ethanolamine, and the like.

The alcohol compounds which can be generally employed in the practice of the invention are monohydroxylic compounds having from 1 to about 6 carbon atoms such as ethanol, isopropanol, butanols, pentanols and the like. Also applicable are those diols represented by the formula above illustrated wherein R and R' are the same or different and are hydrogen or a lower alkyl radical, x is 0 and Z is OH. Exemplary suitable compounds are ethylene glycol, 1,2-propanediol, 1,2- and 2,3-butanediols and the like.

The alkyleneamines which are applicable for use in accordance with the present invention are those represented by the formula:

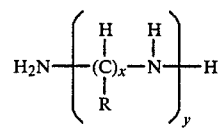

where R is hydrogen or a lower alkyl radical, x is a number from 2 to about 6 and y is a number from 1 to about 4. Preferably the alkyleneamine has an unbranched alkylene moiety. The most preferred alkyleneamine compound is ethylenediamine.

The linear polyalkylene polyamines that are produced in accordance with the present invention can be represented by the formula:

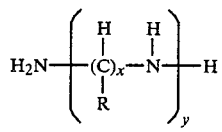

wherein R is hydrogen or a lower alkyl radical, x is a number from 2 to about 6 and y is a number from 2 to about 6. Exemplary compounds corresponding to the above formula include diethylenetriamine, triethylenetetramine, tetraethylenepentamine, pentaethylenehexamine, hexaethyleneheptamine and the like.

In accordance with the process of the invention the particular reactants applicable for use, as hereinabove described, are reacted in the presence of a derivative of carbonic acid at an elevated temperature at which the reaction will proceed under pressures sufficient to maintain the reaction mixture substantially in a liquid phase. The proportions of amine and alkanolamine reactants employed may vary over a wide range. In general, however, the amine and alkanolamine are utilized in molar ratios of from about 1:2 to about 20:1, and preferably, in a molar ratio of from about 1:1 to about 4:1.

Suitable derivatives of carbonic acid which can be employed in accordance with the present invention include, for example, carbon dioxide or a compound formed by the addition of an amine or alcohol to carbon dioxide, provided that such addition compound can enter into an exchange or metathesis process with an amine or alcohol reactant to form an equilibrium concentration of a urea, carbonate, or carbamate of the reactant molecule. Such addition compounds include, for example, carbon dioxide, carbonic acid diamides (ureas), carbonic acid diesters (organic carbonates), carbonic acid half-ester/half amides (carbamic acids and organic carbamates), carbamate and carbonate salts, and the like, and mixtures of any of the above.

More particularly, suitable carbonic acid diamides include urea and ethyleneurea.

Suitable carbonic acid diesters include dimethyl carbonate and ethylene carbonate.

In addition, suitable carbamic acids and carbamates (half-amide/half-esters) include ethyl carbamate, methyl dimethylcarbamate, and 2-oxazolidinone.

Further, suitable carbamate and carbonate salts include potassium dimethylcarbamate, potassium carbonate, sodium bicarbonate, ammonium carbonate, ethylenediamine carbonate, and potassium ethyl carbonate.

The above-mentioned derivatives of carbonic acid are not intended to be exhaustive of those which may be employed in the process of the present invention. The materials are set forth to illustrate types of derivatives of carbonic acid that will be effective in the process of the invention. It is generally desirable to avoid introducing into the reaction mixture amines and alcohols other than primary reactants as described above. Therefore it is often convenient to use as catalyst a carbonic acid derivative formerly derived from one of the reacting amines or alcohols. For example, if the reaction is to use ethylenediamine, then ethyleneurea would be a preferred catalyst. Similarly, 2-oxazolidinone and urea would be especially suitable catalysts for reactions of monoethanolamine and ammonia, respectively.

The amount of carbonic acid derivative compound employed in the process of the invention is not critical and can vary widely depending upon the particular reactants present and reaction conditions employed. Only a small amount of carbonic acid derivative compound is required to effect the reaction between the reactants resulting in the formation of predominantly linear (non-cyclic) polyalkylene polyamines. In general, at least about 0.02 mole of carbonic acid derivative per mole of alkyleneamine or ammonia reactant should be present. Although useful conversions of reactants to polyalkylene polyamines may be obtained even with only small amounts of said carbonic acid derivatives, stoichiometric or even excess amounts of carbonic acid derivative may also be used.

The temperature at which the reaction should be carried out is within the range from about 150° C. to a temperature at which decomposition of the reaction products may occur, generally about 350° C. Preferably, the reaction temperature is within the range from about 200° C. to about 300° C. The pressures under which the reaction should be carried out are not critical and can be varied over a wide range though the pressures should be high enough at the reaction temperature to keep the reaction system substantially in the liquid phase.

The reaction is allowed to proceed at the temperature employed until the desired amount of conversion is obtained, in general, within the range of about 0.5 to about 5 hours.

The desired predominantly linear polyalkylene polyamine compounds produced may be recovered from the reaction product mixture by conventional procedures, such as distillation, without difficulty. For example, the reaction product mixture may be directly distilled, or initially filtered to remove the small amounts of formed solids, and then distilled. The reaction product mixture may, in an alternate procedure, be treated with water or an alkali such as potassium hydroxide to liberate polyalkylene polyamines that are formed into carbonic acid derivatives, and the carbon dioxide or carbonic acid salts thus formed may be recovered or recycled before separation of the polyamines by distillation.

In general, the process of the invention can be carried out batchwise or continuously employing well-known batch and continuous process techniques and processing apparatus.

The invention is further described in the Examples which follow. All parts and percentages are by weight unless otherwise specified.

EXAMPLES 1-8

In each of examples 1-8 the reaction was performed by charging the reactants to a stainless steel tube of a 3 cm$^3$ or 75 cm$^3$ capacity. The tube was then sealed and immersed in a fluidized sand bath preheated to the desired reaction temperature. After the reaction was completed, the reactor tube was withdrawn from the heated bath and cooled rapidly by plunging it into cold water. The reactor tube was then opened and its contents were either analyzed directly by gas chromatography or hydrolyzed and then analyzed by gas chromatography.

Hydrolysis of the reaction products, when applicable, was accomplished by refluxing the reaction mixture overnight with 50 percent aqueous potassium hydroxide (8 moles KOH per mole of carbon dioxide or equivalent catalyst charged). The liberated amines were isolated by extraction with isopropanol and concentrated by distillation prior to analysis.

The proportion of reactants in each example 1–8 and the reaction conditions employed are reported in Table I and an analysis of the reaction products obtained in each of the examples 1–8 are summarized in Table II.

The compound abbreviations used in the tables are:
MEA—Monoethanolamine
AEEA—N-(2-aminoethyl)ethanolamine
DEA—Dithanolamine
EDA—Ethylenediamine
PIP—Piperazine
AEP—N-(2-aminoethyl)piperazine
L-TETA—Linear triethylenetetramine
2-IM—2-imidazolidinone
2-OX—2-oxazolidinone

TABLE I

| | Alcohol | | Amine | | Catalyst | | | |
|---|---|---|---|---|---|---|---|---|
| | Type | Amount (gm) | Type | Amount (gm) | Type | Amount (gm) | Temp °C. | Time Hours |
| 1 | MEA | .99 | EDA | .97 | 2-IM | .0698 | 325 | 2 |
| 2 | MEA | .355 | EDA | 1.74 | 2-IM | .100 | 300 | 6 |
| 3 | MEA | 8.0 | EDA | 23.6 | 2-IM | 11.3 | 250 | 3 |
| 4 | DEA | 10.0 | (1) | | UREA | 17.14 | 250 | 1 |
| 5 | AEEA | 12.2 | EDA | 13.9 | 2-IM | 9.90 | 300 | 6 |
| 6 | DEA | 10.0 | (1) | | UREA | 17.14 | 200 | 2 |
| 7 | AEEA | 20.0 | (2) | | (NH$_4$)$_2$CO$_3$ | 27.71 | 275 | 3 |
| 8 | (3) | | DETA | 23.8 | 2-OX | 9.95 | 275 | 4 |

(1) The amine used in this example was in its carbonic acid derivative form as Urea.
(2) The amine used in this example was in its carbonic acid derivative form (NH$_4$)$_2$CO$_3$.
(3) The alcohol used in this example was in its carbonic acid derivative form 2-oxazolidinone.

TABLE II

| | EDA gm | MEA gm | PIP gm | DETA gm | DEA gm | AEEA gm | AEP gm | L-TETA gm |
|---|---|---|---|---|---|---|---|---|
| 1 | .826 | .752 | .020 | .143 | .0 | .075 | .009 | .010 |
| 2 | 1.567 | 0.219 | .005 | .067 | .0 | .004 | .002 | .0 |
| *3 | 31.8 | 6.53 | (1) | 2.32 | .0 | .0 | .0 | .0 |
| *4 | 0.17 | .01 | .01 | 1.35 | .0 | 4.44 | ND | ND |
| *5 | 15.2 | 2.10 | (1) | 0.53 | .0 | 0.58 | 0 | 1.6 |
| *6 | 0.14 | .0 | (1) | 1.26 | .0 | 4.65 | .08 | .10 |
| *7 | 0.28 | 1.55 | (1) | 4.55 | .0 | 0.08 | 0.15 | 0.39 |
| *8 | 5.8 | 0.36 | (1) | 11.08 | .0 | 0.84 | 0.43 | 1.73 |

(1) The product amount was in combination with the MEA; the MEA and PIP were not analyzed for separately.
(2) ND — Not determined
*The product of this reaction was hydrolyzed prior to analysis.

I claim:

1. A process for preparing predominantly linear polyalkylene polyamines which comprises reacting ammonia or an alkyleneamine compound having two primary amino groups or mixtures thereof with an alcohol having primary or secondary hydroxyl groups or an alkanolamine compound having a primary or secondary amino group and a primary or secondary hydroxyl group or mixtures thereof in the presence of a derivative of carbonic acid as a catalyst sufficient to effect the reaction resulting in the formation of predominantly linear polyalkylene polyamines at a temperature at which the reaction will proceed under pressures sufficient to maintain the reaction mixture substantially in the liquid phase; and recovering the polyalkylene polyamines from the product mixture.

2. The process of claim 1 wherein the alkanolamine reactant is represented by the formula:

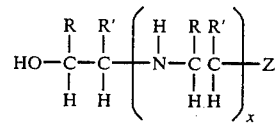

wherein R and R' are the same or different and are hydrogen or a lower alkyl radical, x is an integer from 0 to about 6 and Z is OH or NH$_2$.

3. The process of claim 1 wherein the alcohol reactants are monohydroxylic compounds having from 1 to about 6 carbon atoms or diols having 2 to 4 carbon atoms.

4. The process of claim 2 wherein the alkanolamine is monoethanolamine, diethanolamine or mixtures thereof.

5. The process of claim 3 wherein said alcohol is ethylene glycol.

6. The process of claim 1 wherein said alkyleneamine reactant are those represented by the formula:

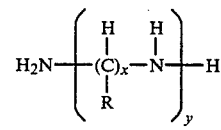

wherein R is hydrogen or a lower alkyl radical, x is a number from 2 to about 6, and y is a number from 1 to about 4.

7. The process of claim 1 wherein said alkyleneamine reactant is ethylenediamine.

8. The process of claim 1 wherein said derivative of carbonic acid is carbon dioxide or a compound formed by the addition of an amine or an alcohol to carbon dioxide which compound can enter into an exchange or metathesis process with an amine or alcohol reactant to form an equilibrium concentration of a urea, carbonate, or carbamate of the reactant molecule.

9. The process of claim 1 wherein at least about 0.02 mole of carbonic acid derivative is provided per mole of alkyleneamine or ammonia.

10. A process for preparing predominantly linear polyalkylene polyamines which comprises reacting ammonia or an alkyleneamine compound having two primary amino groups or mixtures thereof with an alcohol having primary or secondary hydroxyl groups or an alkanolamine compound having a primary or secondary amino group and a primary or secondary hydroxyl group or mixtures thereof in the presence of at least about 0.02 mole of a derivative of carbonic acid per mole of alkyleneamine or ammonia at a temperature at which the reaction will proceed under pressures sufficient to maintain the reaction mixture substantially in a liquid phase; and recovering the polyalkylene polyamines from the product mixture produced.

* * * * *